US006822461B2

(12) United States Patent
Klün (10) Patent No.: US 6,822,461 B2
(45) Date of Patent: Nov. 23, 2004

(54) PROCESS AND DEVICE FOR MEASURING THE STATE OF DEGRADATION OF OILS OR FATS

(75) Inventor: Wolfgang Klün, Ingolstadt (DE)

(73) Assignee: Ebro Electronic GmbH & Co. KG, Ingolstadt (DE)

( * ) Notice: Subject to any disclaimer, the term of this patent is extended or adjusted under 35 U.S.C. 154(b) by 0 days.

(21) Appl. No.: 10/330,451

(22) Filed: Dec. 27, 2002

(65) Prior Publication Data

US 2003/0155935 A1 Aug. 21, 2003

(30) Foreign Application Priority Data

Dec. 28, 2001 (DE) .......................... 101 63 760

(51) Int. Cl.⁷ ............................................ G01R 27/26
(52) U.S. Cl. ...................................... 324/698; 324/71.1
(58) Field of Search .................. 73/53.02; 324/71.1, 324/664, 698; 436/60

(56) References Cited

U.S. PATENT DOCUMENTS

| | | | |
|---|---|---|---|
| 3,739,265 A | 6/1973 | Skildum | 324/61 R |
| 3,746,974 A | 7/1973 | Stoakes et al. | 324/61 R |
| 4,128,006 A | 12/1978 | Grabow | 73/724 |
| 4,586,383 A | 5/1986 | Blomquist | 73/706 |
| 5,540,086 A | 7/1996 | Park et al. | 73/53.05 |
| 5,592,098 A | 1/1997 | Suzuki et al. | 324/663 |
| 5,656,780 A | 8/1997 | Park | 73/724 |
| 5,665,921 A | 9/1997 | Gerst et al. | 73/715 |
| 5,774,056 A | 6/1998 | Berry, III et al. | 340/607 |
| 5,824,889 A | 10/1998 | Park et al. | 73/116 |
| 6,004,442 A | 12/1999 | Choulga et al. | 204/416 |
| 6,282,947 B1 * | 9/2001 | Schon et al. | 73/53.01 |
| 6,308,574 B1 | 10/2001 | Klün et al. | 73/706 |
| 6,373,263 B1 * | 4/2002 | Netzer | 324/665 |
| 6,469,521 B1 | 10/2002 | Klun et al. | 324/658 |
| 6,543,292 B1 * | 4/2003 | Colton et al. | 73/723 |
| 6,600,306 B1 * | 7/2003 | Pernot et al. | 324/71.1 |
| 6,617,968 B1 * | 9/2003 | Odisho et al. | 340/450.3 |
| 6,694,285 B1 * | 2/2004 | Choe et al. | 702/182 |
| 2004/0060344 A1 * | 4/2004 | Kauffman et al. | 73/53.01 |

FOREIGN PATENT DOCUMENTS

| | | | |
|---|---|---|---|
| DE | 3732100 A1 | 4/1989 | G01L/11/00 |
| DE | 40 31 981 A1 | 4/1992 | G08C/17/00 |
| DE | 196 08 422 A1 | 9/1997 | G01L/9/00 |
| DE | 196 37 763 A1 | 3/1998 | G01L/19/14 |
| DE | 198 16 872 A1 | 10/1999 | G01L/7/00 |
| DE | 198 29 415 A1 | 1/2000 | |
| DE | 100 15516 A1 | 11/2000 | |
| EP | 0 736 757 A1 | 10/1996 | G01L/19/06 |
| EP | 1 046 908 A2 | 3/2000 | |

* cited by examiner

Primary Examiner—Anjan Deb
Assistant Examiner—Walter Benson
(74) Attorney, Agent, or Firm—Fish & Richardson P.C.

(57) ABSTRACT

The present invention relates to a process and device for the monitoring of fats and oils in the preparation of food, which provide for the exchange of oil or fat in a timely manner, before they have become harmful for human consumption. The proposed process for measurement distinguishes itself by the fact that the measurement is already taking place during the temperature adaptation of the sensor, whereby a measurement can take place which is particularly fast and thus suitable for use in practice. Along with this, the device is formed in such a manner that disturbances of the measurement can be largely eliminated.

26 Claims, 3 Drawing Sheets

PROCESS AND DEVICE FOR MEASURING THE STATE OF DEGRADATION OF OILS OR FATS

FIELD OF THE INVENTION

The present invention relates to a process for measuring the state of degradation of oils or fats. Also disclosed is a device for measuring the state of degradation of oils or fats.

BACKGROUND OF THE INVENTION

The significance of the preparation of food with the aid of hot oils or fats is gaining importance amongst the public. Through the use of these hot substances, the cooking time for the preparation of many dishes is significantly shortened in comparison to other processes. In addition, the fats or oils used in the preparation may be used over a longer period of time for the cooking of larger amounts of food since the consumption of the hot oil in deep-frying is relatively small. However, this advantage of longer use of oils or fats also brings with it a disadvantage, since oils and fats, when used at the customary hot temperatures between approximately 90° C. to 180° C., are substantially changed in their composition i.e., decomposed or degraded.

The decomposition of oils and fats during the cooking process, essentially take place through the oxidation of the oil or the fat, during which many undesired chemical products arise such as, for example, polymers or free fatty acids. These undesired products negatively affect the taste of the prepared dishes, and also have a negative effect on the quality of the deep-fried food with respect to the health of the consumer.

It is therefore necessary to replace the oils and fats used for human consumption regularly and in a timely manner in order to avoid the negative effects on the consumer. In practice however, the oils and fats are replaced too early or too late. The criteria for the replacement are, in practice, frequently of a subjective nature, where replacement of the oil or fat is usually carried out according to time criteria or based on a visual or olfactory change in the oil or fat.

In order to be able perform the replacement of oils and fats in a timely manner, it is necessary to determine the quality of the fat according to objective criteria, i.e., when the decomposition of the fat or oil has progressed so far thereby requiring replacement.

The prior art (U.S. Pat. No. 3,739,265) provides a process and a device which provide for examining the oil for its electrical properties, in particular its dielectric properties. For this purpose, the measuring device has a receiving space in the form of a key which has disposed at its base a sensor formed as a capacitor. For the measurement, a certain amount of oil is applied to the sensor and the capacitance measured with this system is processed in an electrical circuit. As a result a measured value is obtained which provides information concerning the degree of decomposition of the fat. For this, a comparison is carried out between the fat or oil to be tested and a standard liquid which is also measured in an additional measuring process, usually beforehand. The dielectric constant, or change of the dielectric constant, which the sensor determines in the process, is a measure for the degree of decomposition of the fat or oil.

EP 1 046 908 A2 teaches a process and a device for measuring the state of oils or fats by measuring an electrical property of the oil or fat, using a measuring head that is disposed on an attachment of the measuring device. This is suitable for dipping into the hot fat or oil, e.g., in a deep-fat fryer, during operation in order in so doing to measure the capacitive properties of the oil.

U.S. Pat No. 3,739,265 teaches an instrument which requires the oil to be filled into a receiving device prior to measurement, for which purpose the oil must first be removed from the deep-fat fryer. Subsequently, the electrical properties of the oil or fat are measured in the device. For determining the state of the oil or fat, this device is not suitable for use in practice, i.e., even during the time when a kitchen is in operation. In particular, the complexity of the handling technology and the expenditure of time do not allow for practical application.

The device disclosed in EP 1 046 908 A2 is suitable for measuring the state of the oil directly during the operation, for example, of a deep-fat fryer. For this purpose, the sensor, which is disposed on an attachment of the device, is dipped directly into the hot oil or fat. After the dipping it is necessary for the exact determination of the measured value, and also for the determination of the temperature of the oil, to wait a certain time until a measurement providing information can be performed. The electrical connection between the sensor and the evaluation electronics occurs via cable laid free in the interior of the attachment.

SUMMARY OF THE INVENTION

"It is an object of the present invention to provide a process for measuring the state of degradation of oils and fats in order to make the process and device more suitable for use in practice and, in particular, to shorten the measuring time, to improve the result of the measurement, and to minimize the variability of the measurement. An embodiment of the invention provides a device for measuring the state of degradation of oil or fat comprising a sensor for measuring an electrical property of the oils or fats, wherein the sensor is mounted on a carrier and is connected to measurement electronics via one or more electrical leads, and further comprising a housing for evaluating or displaying the result of the measurement, wherein at least one of the electrical leads is disposed on a carrier part."

It is also an object of the present invention to provide a device for measuring the state of degradation of oils and fats. An embodiment of the invention provides a process for measuring the state of degradation of oil or fat comprising, measuring the dielectric constant of oil or fat with a sensor, wherein the sensor is brought into contact with the oil or fat in a liquid state, wherein the sensor is at a lower temperature than the oil or fat, and the dielectric constant of the oil or fat is measured while the sensor is adapting to the temperature of the oil or fat.

BRIEF DESCRIPTION OF THE DRAWINGS

The invention will be better understood by reference to the following detailed description of the preferred exemplary embodiments when read in conjunction with the appended drawings.

DESCRIPTION OF EMBODIMENTS

An embodiment of the invention provides a device for measuring the state of degradation of oil or fat comprising a sensor (2) for measuring an electrical property of the oils or fats, wherein the sensor is mounted on a carrier (21) and is connected to measurement electronics (32) via one or more electrical leads (3), and further comprising a housing for evaluating or displaying the result of the measurement, wherein at least one of the electrical leads is disposed on a carrier part (31).

In an embodiment of the invention, at least one of the electrical leads is disposed on a carrier part, in order to minimize variability of the measurements due to the electrical leads. Due to the fact that the leads are disposed in a fixed manner on the carrier part and are not present as free cables in the attachment of the measurement device, their spacing relative to each of the neighboring leads is constant so that their electrical property of forming a capacitor with the neighboring lead is taken into account in such a manner that this effect at least remains constant. Due to the fact that the leads are disposed on the carrier part, they always retain their position, and thus their capacitance, even in case of movement of the measuring device and in case of thermal expansions or other changes of the measuring device, remains constant.

In an embodiment of the invention, the lead can particularly favorably be present as a printed lead on, for example, a carrier part of a stable material. The use of a carrier part therefore makes it possible to advantageously guarantee constant conditions on the measuring device so that a reliable result of measurement can be obtained. Moreover, the carrier part advantageously makes it possible to produce the whole unit in a cost-effective manner, because the constant conditions are always reproducible.

In addition, the carrier part is moreover in the position to accept further improvements, for example, to take on additional electrical leads or switches.

In an embodiment of the invention, the carrier part is formed as one piece with the carrier of the sensor. Thereby it is possible, in a particularly simple manner, to connect the sensor to the electrical leads, since both can be formed, for example, as printed circuits so that connections can be implemented securely and without problems. Moreover, the whole unit becomes more stable, simpler, and cheaper to produce.

It is advantageous if the carrier part carries at least part of the measurement electronics of the measurement device, because thereby, for example, disturbing effects due to free leads can be avoided, even in the area of the electronics itself In an embodiment of the invention, the measurement electronics can be advantageously disposed on the carrier part, whose fixed disposition of its elements contributes to minimizing the variability of the measurement.

In an embodiment of the invention, the measurement device is equipped with a sensor which is formed as a capacitor. The dielectric constants of the oils or fats are measured with the aid of a capacitor, said dielectric constants then representing a measure of the state of the fats or oils. In so doing, the capacitor is particularly advantageously formed as an interdigital capacitor (IDC), since this makes possible a particularly reliable measurement of the dielectric constant and is not sensitive with respect to disturbing effects. In an embodiment, the carrier part is produced from a non-metallic material, since thereby it can be used as the holder of an electrical lead and at the same time an insulator with respect to the neighboring electrical lead. In particular, a carrier part of a non-metallic material is thus particularly suitable.

Along with this, a carrier part of ceramics is particularly advantageous since the ceramics are mechanically strong as well as particularly suitable for a printed lead. Moreover, ceramics are not sensitive to temperature and are extremely stable in form, even in the case of changes in temperature, whereby the disturbing effects on leads mounted on it are extremely small.

An embodiment of the invention teaches a measuring device, wherein the sensor is disposed on a carrier and is fastened via its carrier to the attachment of the housing, where the fastening means thermally separates the sensor and the attachment, and the fastening means separates the carrier from the attachment, so that the adaptation of the carrier and of the sensor to the temperature of the material to be measured is not significantly affected by the attachment, it is advantageously achieved that the measurement value measured by the sensor is not disturbed by the effects of temperature. Through this advantageous development of the measuring device it is achieved that the attachment to the carrier draws as little heat as possible while the carrier is adapting its temperature to the material to be measured in the course of the measurement.

The thermal separation allows the carrier to adapt quickly to the temperature of the material to be measured, independently of the structure of the attachment and its thermal capacity. Along with that, the fastening means is constructed in such a manner that it mechanically separates the attachment from the carrier, so that no heat can be transferred directly from the carrier to the attachment. Through the structure of the fastening means, e.g., via its small spatial extension, its property of thermal separation can be improved still further.

In an embodiment of the invention, the fastening means is provided with an essentially low thermal conductivity. Along with this advantageous effect on the measurement, a reliable connection between the carrier of the sensor and the attachment of the housing can moreover be achieved with a measurement device developed according to the invention. Furthermore, alignment errors and dimensional tolerances can be advantageously compensated by a fastening means between the carrier and attachment of the housing.

Particularly beneficial is the development of the fastening means as a sealing means between the carrier and the attachment, so that the penetration of fat or oil into the interior of the attachment can be prevented. For this purpose, the sealing means is disposed in the entire area between the carrier and the attachment.

In an embodiment of the invention, the fastening means is formed as an adhesive. Through the disposition of the adhesive between the carrier and the attachment, a reliable fastening of the carrier to the attachment is achieved after the setting of the adhesive. In addition, this type of fastening is cost-effective and quickly mounted and has no effect on the measuring device or on its results of measurement. Particularly beneficial is the use of an adhesive in which the connection, after setting, forms a mechanical connection between attachment and carrier, said mechanical connection being elastic. Thereby it is achieved that thermal stresses which occur in the dipping of the sensor into hot oil or fat can be absorbed by the fastening means and no disturbances of the connection between attachment and carrier occur. In the case where the adhesive simultaneously forms the sealing means, no gap between sealing means and attachment can occur.

In an embodiment of the invention, the fastening means is formed as an adhesive which, after setting, forms the fastening means between the carrier and the attachment of the housing. Through the use of an adhesive a particularly simple structure of the fastening means can be realized which is cost-efficient and can be produced quickly. Due to the fact that the adhesive, after setting, forms a mechanical connection between carrier and attachment, said mechanical connection being elastic, it is particularly advantageously guaranteed that the carrier can extend undisturbed from the attachment in case of a temperature change, and contract once again, without stresses between carrier and attachment occurring. Moreover, shaking or impacts which are exerted on the attachment are compensated by an elastic fastening means.

In an embodiment of the invention, the adhesive or the fastening means is generally developed with a thermal conductivity of less than 1 watts/m °K, preferably less than 0.1 watts/m °K. Through this formation of the fastening means or the adhesive, a particularly good thermal separation between the attachment and the carrier can be achieved so that the effects on the measured value which are due to a change in temperature during the measurement can be kept very small. An embodiment of the invention is characterized by the fact that the adhesive is a silicone adhesive which, along with the aforementioned properties, can be introduced advantageously for use in connection with food.

In an embodiment of the invention, the sensor is disposed on a carrier which has a thermal conductivity of less than 9 watts/m °K, preferably less than 3 watts/m °K. Thereby it is guaranteed that the effects on the measurement which are due to the change in temperature can be kept small. For this purpose, the carrier is formed from a ceramic material.

In an embodiment of the invention, the sensor is surrounded by a shielding which shields the sensor against effects on its capacitive properties which are due to the environment at the point of measurement. Thereby it is achieved that so-called straying capacitances are largely shielded so that they have no effect on the measurement of capacitance. Through the shielding it is therefore achieved that the dielectric constant measured by the sensor of the measuring device is not disturbed by the effects on the capacitance of the sensor which are due to the environment.

It is advantageous if the shielding is disposed essentially in the plane in which the sensor extends and at least partially surrounds the sensor in this plane. Thereby the greatest part of the straying capacitances is shielded from the sensor so that its capacitance practically does not vary as a function of the area where the sensor is introduced into the material to be measured. For this purpose, the shielding is advantageously formed of a metallic material since this is particularly suitable for shielding off, at least for the most part, the effects on the sensor of the measurement device which are due to the environment at the point of measurement.

In an embodiment of the invention, the shielding is formed at least partially by a continuation of the attachment of the measuring device. Through this development it is possible to develop a beneficial, form-conserving, and effective shielding in the area of the sensor of the measuring device. This can, for example, advantageously be realized by a flattening of a tubular attachment, where the flattening then lies in a plane and contains a free space in which the sensor is disposed in a horizontal position in the plane of the shielding.

In an embodiment of the invention, a temperature probe, preferably in the form of an ohmic resistor, e.g., particularly advantageously of platinum, is formed on the sensor along with the sensor. Thereby the measuring device can record the temperature of the material to be measured simultaneously with the measurement of the dielectric constant and draw on the measured value for the determination of the quality of the oil or fat.

In an embodiment of the invention, the measurement process can be carried out at a high level of speed. By measuring the dielectric constant of the material to be measured even while the sensor is adapting to the temperature of the material to be measured, the measurement can be performed without waiting for the temperature of the sensor to completely adapt to the temperature of the material to be measured.

The sensor can therefore advantageously be used for the measurement at its current temperature, e.g., the ambient temperature, just as the material to be measured can be drawn on for the measurement at its normal temperature. This is particularly advantageous because in most cases the oil or fat are not present in liquid form as long as it is at the ambient temperature. This makes it possible, however, to perform the measurement when the material to be measured is at its ordinary temperature, which is the case most of the time. Also in this way, checks of the food plants by the authorities are possible without any measures having to be introduced in advance for this purpose because in the case of a measurement with the process according to the invention no preparations with respect to the material to be measured have to be carried out.

The measurement can been performed long before the sensor has assumed the temperature of the material to be measured. In so doing, a fixed value at which the measurement takes place, e.g., 80° C. or 90° C., may be predefined. At such a temperature practically all the fats or oils which are used in the food industry are in the liquid state so that the determination of the dielectric constant at such a temperature is possible in any case. In other respects this advantageous extension of the invention offers the possibility of shortening the time of the measuring process since the determination of the dielectric constant has already taken place early in the phase of adaptation of the sensor to the temperature of the material to be measured.

An embodiment of the invention provides a process for measuring the state of degradation of oil or fat comprising, measuring the dielectric constant of oil or fat with a sensor, wherein the sensor is brought into contact with the oil or fat in a liquid state, wherein the sensor is at a lower temperature than the oil or fat, and the dielectric constant of the oil or fat is measured while the sensor is adapting to the temperature of the oil or fat.

The process according to the invention is advantageous if, during the measurement, an on-going monitoring of the temperature of the material to be measured is taking place, so that at any time the measuring device is oriented relative to what phase of the temperature adaptation to the material to be measured the sensor is in. Thereby it is advantageously possible to monitor the curve of temperature over time for the adaptation of the sensor to the temperature of the material to be measured and to draw on the present curve of the temperature adaptation for evaluating the result of the measurement, for example, in order to deduce the temperature of the material to be measured from the curve over time of the adaptation. Thereby the temperature of the material to be measured can be determined without having to wait for the sensor's complete temperature adaptation to the material to be measured.

Thereby it is advantageously possible to monitor a check of the measured and determined values of the dielectric constant and the state of the material to be measured and to test their plausibility. Therefore the result of the measurement can be further refined thereby. Additional advantageous developments of the invention are described in the parallel and subordinate claims as well as in the presentation of the invention with the aid of graphic representations.

Figure 1:
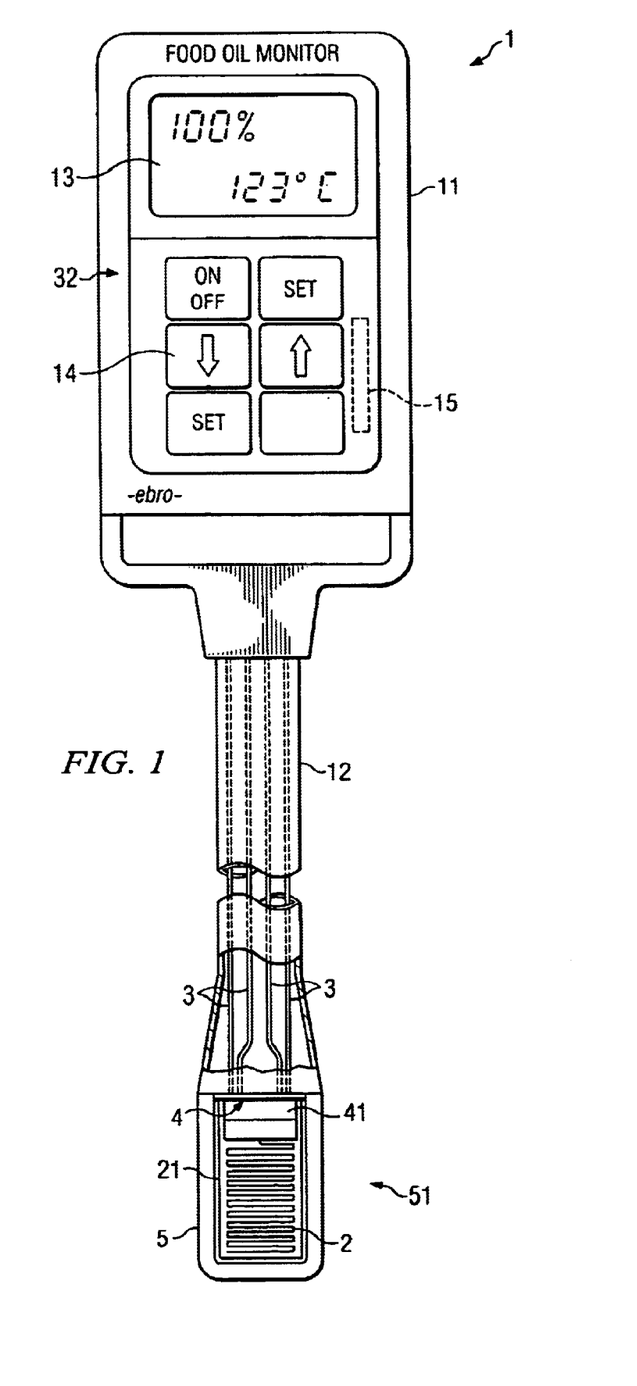
FIG. 1 is a measuring device, for measuring the state of a material to be measured, with a housing and a display for the result of the measurement.

FIG. 1 shows a measuring device 1 according to the invention, for measuring the state of oils or fats, consisting essentially of the housing 11, which contains the measurement electronics 32, and the attachment 12, which holds, on its side facing away from the housing 11 and via a fastening means 4, the carrier 21 on which the sensor 2 in turn is mounted. The sensor 2 is connected to the measurement electronics 32 via electrical leads 3 running in the interior of the attachment 12 (represented as dashed lines). The sensor 2 and its carrier 21 are surrounded by a shielding 5, which is formed as a continuation 51 of the attachment 12 (cf FIG. 3).

The housing 11 contains a display 13, visible from outside, for displaying the measured value which results at the end of the measurement. The display 13 is made in the form of an LCD display and can be switched between different displays, according to the operation of the measuring device 1, for easier understanding by the user. Thus it is possible, for example, to set the measuring device 1 to a representation which gives the state of the oil or fat in the form of a percentage value, or to set the display so that a graphic representation illustrates the state of the material to be measured. The switching to different types of display is accomplished via a keyboard 14 with whose aid the apparatus can be operated, controlled, and programmed.

Moreover, installed on the housing, there is an interface 15 with whose aid data, which, for example, are stored in the measurement electronics 32 of the measurement device 1, can be read out, and also data from outside, e.g., a PC, can be read into the measuring device 1. The keyboard 14 can be formed, for example, as a keypad. The housing 11, as well as forming the holder for the devices for operation and the reading out of the results of the measurement, also forms, at the same time, the grip for the grasping and holding of the measurement device during the determination of the quality of the oil or fat.

Above the attachment 12, a sufficient clearance, between the housing 11 and the hot material to be measured, it is guaranteed, so that the sensor of the measuring device I can be held in the hot material to be measured by the operator without risk. In order to protect the sensitive measurement electronics 32 from the heat of the material to be measured, the attachment 12 has a sufficient length and it moreover formed of a material with poor thermal conductivity. In the present case, the attachment is expediently formed of stainless steel, which, although a metal, conducts heat relatively poorly. In addition, stainless steel has the advantage that it can be brought into contact with food without problems. The attachment 12 is formed as a tubular component into which the carrier 21 of the sensor 2 is introduced at the end facing away from the housing 11, fastened by means of a fastening means 4, and sealed via a sealing means 41 against the penetration of the material to be measured.

Figure 2:
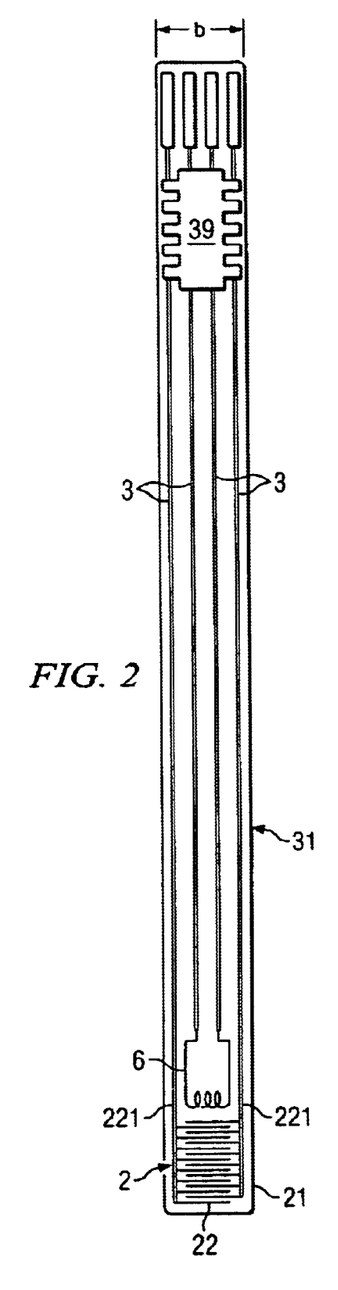
FIG. 2 shows carrier part formed according to an embodiment of the invention with electrical leads disposed thereon, wherein said carrier part is formed as one piece with the carrier for the sensor.

FIG. 2 shows a carrier part 31 formed according to the invention, on which carrier part the electrical leads 3, which connect the sensor 2 to the measurement electronics, are disposed. The carrier part 31 consists of a ceramic component which has a length which reaches from the attachment 12 on which the sensor 2 is disposed, through the attachment 12, and up into the housing 11 of the measuring device 1. Its width b is adapted to the width of the sensor 2. Its thickness is essentially less than its width b and is between about 1 mm and 3 mm. The dimensions are determined essentially according to the demands which are made on the electrical leads 3, according to the length of the attachment 12, and according to the requirements for mechanical strength.

As can be seen from FIG. 2, in the case of a preferred embodiment of the carrier part 31, it is formed as one piece with the carrier 21 of the sensor 2. Carrier 21 and carrier part 31 are therefore both of ceramics and consist of one piece. In the area of the carrier 21, the sensor 2 is mounted, which consists of gold wires finely toothed in one another, whereby a capacitor 22 is formed which is also designated in a special case as an interdigital capacitor 22. The two electrical connections 221 of the capacitor 22 pass over, as one piece, into the corresponding electrical leads 3 and are connected at their other end to the measurement electronics (32), which is in part, namely the preamplifier (39), directly disposed on the carrier part (31).

The electrical leads 3 as well as the capacitor 22 may consist of a fine gold coating on the carrier 21 or the carrier part 31, where this coating is printed directly onto the ceramic component. Due to the fact that ceramics is an electrical non-conductor, the electrical leads as well as the fingers of the interdigital capacitor are electrically insulated against one another.

"Along with the sensor 2, a temperature probe 6 is disposed on the carrier 21 in the immediate vicinity of the capacitor 22. It is formed as an electrical resistor which, in the present case of embodiment, is formed of platinum Also the temperature probe 6 is connected by means of electrical leads 3, as the capacitor 22 also, so that, at the end of the carrier part 31, the leads 3 connected to the temperature probe 6 can in turn be connected to the measurement electronics. By disposing the temperature sensor in the immediate spatial vicinity of the capacitor 22, the temperature probe 6 is suitable for determining the temperature of the capacitor 22 itself in particular, for the reason that the temperature probe 6 and the capacitor 22 are both simultaneously disposed on the carrier 21."

Figure 3:
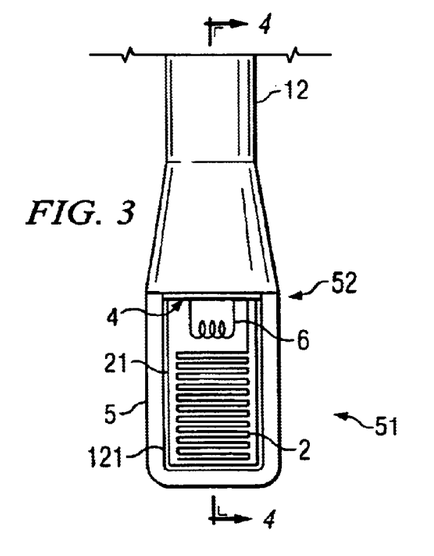
FIG. 3 shows a detail view of the carrier, mounted in an attachment.

FIG. 3 shows the end, facing away from the housing 11, of the attachment 12 with, disposed in the attachment, a carrier 21 on which a sensor 2, as well as a temperature probe 6, are disposed. In the area of the sensor 2, the tubular attachment 12 is pressed flat so that the tubular attachment 12 turns into a flat component. This therefore encloses the carrier 21 laterally. In order that the sensor can lie free, the flat part of the attachment 12 is provided with a punch-out 121 so that, of the attachment 12, there ultimately remains only an area surrounding the carrier 21 on its flat side, said area forming the shielding 5 for the sensor 2 (cf for this also the side view of FIGS. 3 and 4). In the area 52, in which the flat-pressed continuation 51 of the attachment 12 is tangential to the carrier 21, a fastening means 4 is disposed between the continuation 51 of the attachment 12 and the carrier 21, said fastening means extending between the carrier 21 and the continuation 51 of the attachment 12. The fastening means 4 lies between the attachment 12 and the carrier 21 so that the carrier 21 and the attachment 12 cannot touch directly and thus are insulated from one another. The fastening means 4 is formed here as an adhesive injected between the attachment 12 and the carrier 21, said adhesive, after it has hardened, guaranteeing a secure mounting of the carrier 21 on the attachment 12, where at the same time the connection is elastic, the fastening means 4 is a sealing means 41, and a sealing of the area 52 of the attachment 12 forms so that no material to be measured can get, between the attachment 12 and the carrier 21, into the interior of the attachment 12 and thus into the interior of the measuring device 1.

Preferably the fastening means 4 is formed as a silicone adhesive which, after it has hardened or set, advantageously performs both functions, namely that of a fastening means and that of a sealing means. Moreover, a silicone adhesive is still suitable for withstanding high temperatures and moreover it is food-safe, i.e., suitable for use in connection with food.

The shielding 5 encloses the sensor, in the area in which the carrier extends, on three sides, while the fourth side shields, in the area 52 at least partially, due to the fact that here the attachment 12 extends on the upper as well as on the lower side of the carrier 21. The embodiment example of the shielding 5, which FIG. 3 shows, is only one advantageous development. It can also be realized, for example, entirely by a separate wire strap. It is important that the function of shielding straying capacitances, at least partially, is also fulfilled.

An additional beneficial property of a shielding formed in such a manner consists of the fact that it simultaneously forms a mechanical protection for the carrier 21, and thus the sensor 2. On introduction of the measuring device into a container it can therefore be prevented that the sensor or the carrier 21 strikes the wall or the base of the vessel. Along with a development as shown in FIGS. 3 and 4, the shielding 5 can also be formed in such a manner that it is not only disposed in the plane in which the carrier 21 lies but rather spatially more or less surrounds the sensor.

Figure 4:
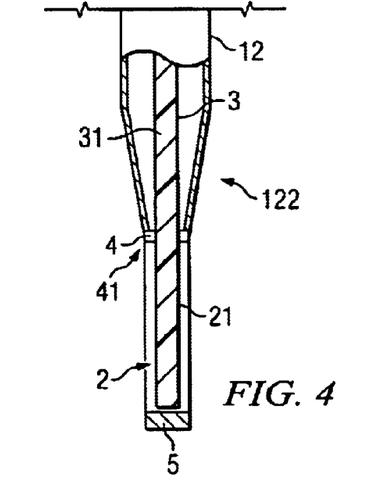
"FIG. 4 shows a section view taken along line B—B of FIG. 3."

FIG. 4 shows a side view of the partial representation of the attachment 12 of FIG. 3. In FIG. 4 the beveling 122 is to be seen which has a counterpart on the opposite side. Through the beveling 122 the wall of the attachment 12 approaches the carrier 21. The fastening means 4, the hardened silicone adhesive, is shown between the walls of the attachment 12. Thereby a mechanical and thermal insulation between the attachment 12 and the carrier 21 is achieved. As already described above, the fastening means 4 simultaneously forms a sealing means 41 between the carrier 21 and the wall of the attachment 12 so that penetration of the material to be measured into the interior of the attachment 12 is reliably prevented.

Figure 5:
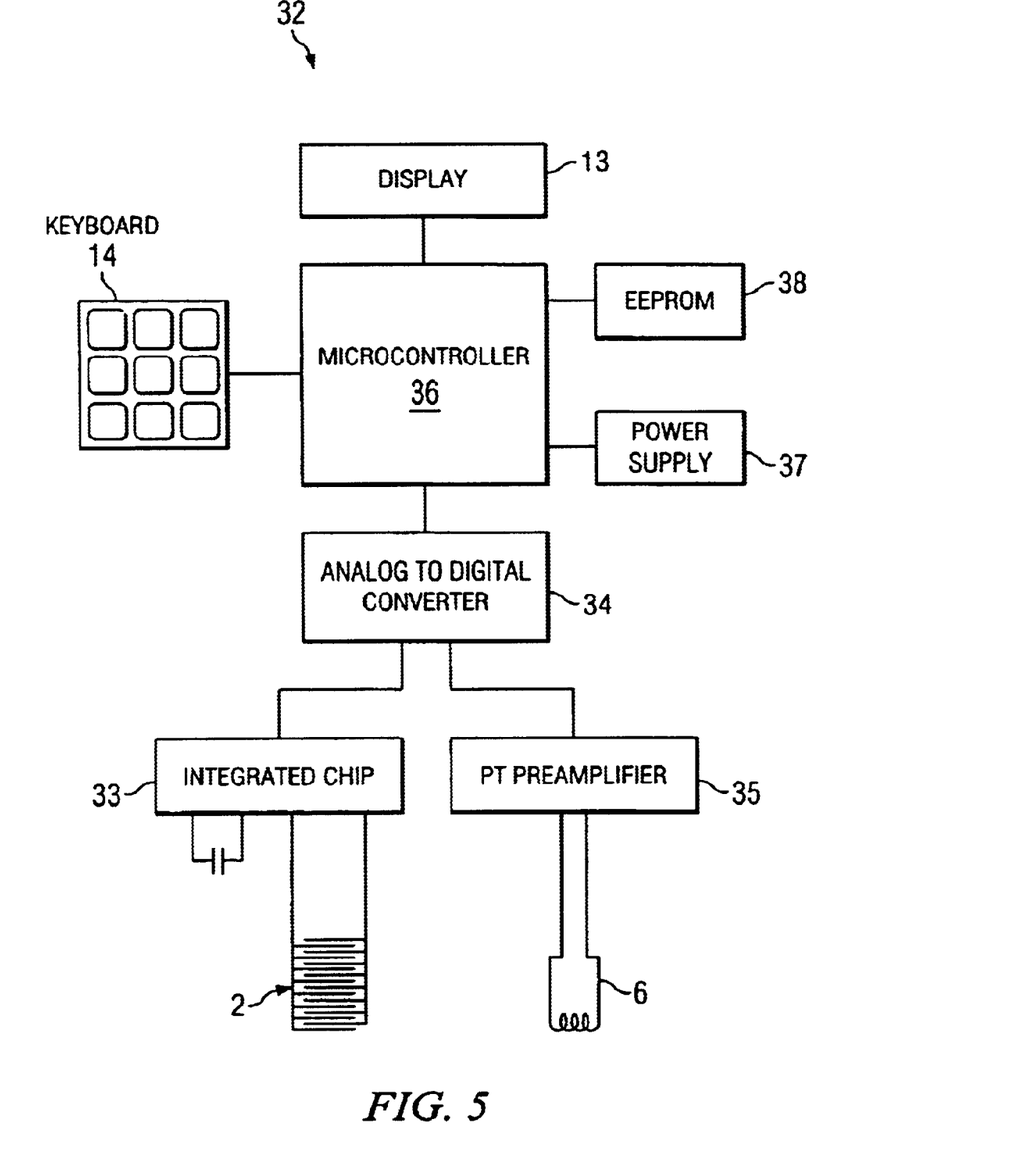
FIG. 5 shows a schematic representation of the sensor and measurement electronics.

FIG. 5 shows a block circuit diagram of the measurement electronics 32 for the measuring device according to the invention as well as for carrying out the process according to the invention. An integrated chip 33, to which the sensor 2 is connected in a half-bridge configuration, is used for measuring the capacitance of sensor 2. The integrated chip 33 produces a measurement frequency in the range of 50 kHz and converts the frequency resulting as a function of the capacitance, into a voltage signal. This voltage signal is subsequently digitized by an analog-to-digital converter 34.

The integrated chip 33 contains moreover a filter for the suppression of 50/60 Hz hum. Moreover, the integrated chip 33 is structured in such a way that it automatically recalibrates the offset as well as the amplification. As can be seen from FIG. 5, the signal of the temperature probe 6 is prepared by a PT preamplifier 35 and subsequently converted into a digital signal via the analog-digital converter 34. The digital signals from the integrated chip as well as from the preamplifier 35 of the temperature probe 6 are then subsequently processed in the microcontroller 36 for carrying out the process according to the invention in the present application. As can be seen from FIG. 5, the microcontroller is supplied with a direct current voltage via a power supply 37. Moreover, the microcontroller 36 is also connected to an EEPROM 38 as well as to the elements already described in FIG. 1, the keyboard 14, and the display 13, which is realized as an LC display.

Along with this, the measuring device works according to the measurement process corresponding to the present invention in such a way that, after the dipping of the sensor of the measurement device into the hot material to be measured, the dielectric constant of the oil is already being measured during the rise, that is, the adaptation of the temperature of the sensor to that of the material to be measured. In so doing, the measurement takes place at a fixed temperature, which, for example, may be between 70° C. and 90° C., more preferably at about 80° C. Moreover, the course of the increase in temperature is measured simultaneously, for which purpose the temperature sensor on the carrier 21 of the measuring device 1 is used. From the curve of the increase in temperature, the actual value of the temperature of the present material to be measured can be determined by extrapolation. With the aid of the value of the dielectric constant measured at a sensor temperature of 80° C. and the actual temperature of the material to be measured, said actual temperature being determined through extrapolation, the actual dielectric constant of the material to be measured is determined at its present actual temperature and, with the aid of the reference values for the oil present which are stored in the EEPROM of the measurement electronics 32, the instantaneous degree of decomposition of said oil is determined. This is then provided as the result in the display 13 of the measurement device 1.

The advantages of the process described lie, in particular, in the fact that a rapid measurement can take place since it is not necessary to first wait until the sensor of the measurement device 1 has reached the actual temperature of the material to be measured. This has the advantage that it is not necessary to wait a relatively long time, in the range of more than a minute, and for the most part more than two minutes, until a measurement can be taken. This makes possible a measuring device which is particularly suitable for use in practice, because long measurement times lead to other effects on the measurement electronics which are due to temperature, said effects ultimately no longer being compensatable and ultimately leading to a device which is not suitable for use in practice.

Because of the nature of the material to be measured, namely of cooking oils and fats which have different properties, i.e., also different dielectric constants, according to their composition and the origin of the oil or fat, it is necessary for the success of the determination of the exact state of the material to be measured that, for the measurement process of the evaluation electronics, reference data be made available, which consist essentially of an association of dielectric constants with a temperature of the material to be measured, as well as the type of the material to be measured itself At the outset of the measurement it is therefore necessary that the operator, via the keyboard of the evaluation electronics, makes available those base data which indicate which particular sort of material to be measured is supposed to be evaluated. With the aid of these data, the evaluation electronics is then in the position to establish whether the measured value of the dielectric constant provides information that the material to be measured must be replaced or not. Obviously the device according to the invention can also be used to measure and display the dielectric constant directly so that following this, for example, a new oil can be subjected to measurement and, from the change of the dielectric constant, the state of the measured used oil can be determined retroactively by one skilled in the art. However, the usual case is that reference values of various oils and fats are present in the storage of the measurement electronics so that, as a result of the measurement, the evaluation electronics of the measurement device according to the invention can directly provide information about the condition of the material to be measured.

What is claimed is:

1. A device for measuring the state of degradation of oil and fat comprising: a carrier,
   a sensor mounted on the carrier for measuring an electrical property of the oils or fats,
   an attachment formed as a tubular component,
   a carrier part disposed inside said attachment,
   measurement electronics connected to the sensor via one or more electrical leads, wherein at least one of the electrical leads is disposed on the carrier part.

2. The device of claim 1, wherein the carrier is formed as one piece with the carrier part.

3. The device of claim 1, wherein at least part of the measurement electronics is disposed on the carrier part.

4. The device of claim 1, wherein the sensor comprises a capacitor.

5. The device of claim 1, wherein the capacitor comprises an interdigital capacitor (IDC).

6. The device of claim 1, wherein the carrier part is made of a non-metallic material.

7. The device of claim 1, wherein the carrier part is made of a non-conducting material.

8. The device of claim 1, wherein the carrier part is made of ceramics.

9. The device of claim 1, wherein the one or more electrical leads are printed on the carrier part.

10. A device for measuring the state of degradation of oil or fat at a temperature comprising:
    a carrier;
    a sensor for measuring an electrical property of the oil or fat;
    a housing comprising electronics for evaluating or displaying a result of measuring the electrical property;
    an attachment attaching the sensor to the housing; and
    fastening means for fastening the carrier to the attachment, wherein the fastening means thermally separates the sensor disposed on the carrier and the attachment such that adaptation of the carrier and the sensor to the temperature of the oils or fats to be measured is not significantly affected by the attachment.

11. The device of claim 10, wherein the fastening means comprises a seal against the entry of fat or oil into the attachment.

12. The device of claim 10, wherein the fastening means is an adhesive.

13. The device of claim 12, wherein the adhesive forms a mechanical connection between the carrier and the attachment, said mechanical connection being elastic.

14. The device of claim 12, wherein the adhesive has a thermal conductivity of less than 1 W/mK.

15. The device of claim 14, wherein the adhesive has a thermal conductivity of less than 0.1 W/mK.

16. The device of claim 12, wherein the adhesive is a silicone adhesive.

17. The device of claim 10, wherein the sensor is connected to the attachment via the carrier, and wherein the carrier has a thermal conductivity of less than 10 W/mK.

18. The device of claim 17, wherein the carrier has a thermal conductivity of less than 5 W/mK.

19. The device of claim 10, wherein the carrier is a ceramic component.

20. The device of claim 10, comprising a shield surrounding the sensor, wherein the sensor comprises capacitive properties and the shield protects the sensor against effects on the capacitive properties of the sensor that are due to the environment at the point of measurement.

21. The device of claim 20, wherein the shield and the sensors are disposed in a common plane.

22. The device of claim 20, wherein the shield comprises a metallic material.

23. The device of claim 20, wherein the shield is formed by a continuation of the attachment.

24. The device of claim 10, wherein a temperature probe is disposed on the carrier.

25. A process of measuring oil or fat comprising:
    bringing a sensor at a temperature into contact with the oil or fat when the oil or fat is in a liquid state and at a higher temperature than the temperature of the sensor;
    measuring the dielectric constant of the oil or fat before the temperature of the sensor reaches the higher temperature of the oil or fat;
    measuring the temperature of the sensor while the sensor is adapting to the higher temperature of the oil or fat;
    determining the higher temperature of the oil or fat from the measured temperatures of the sensor before the temperature of the sensor reaches the higher temperature of the oil or fat; and
    using reference values in memory of a measurement device comprising the sensor to determine the dielectric constant of the oil or fat before the temperature of the sensor reaches the higher temperature of the oil or fat.

26. A device for measuring the state of oil or fat comprising:
    a housing that can be held by a user;
    measurement electronics in the housing;
    a sensor for measuring an electrical property of the oil or fat, the sensor being connected to the measurement electronics;
    a temperature sensor positioned near the sensor for measuring the temperature of the sensor; and
    memory in the housing connected to the measurement electronics and having stored therein reference values associated with the electrical property of the oil or fat, wherein the reference values aid determining the state of the oil or fat based on measurements of the electrical property of the oil or fat and measurements of the temperature of the sensor.

* * * * *

UNITED STATES PATENT AND TRADEMARK OFFICE
CERTIFICATE OF CORRECTION

PATENT NO. : 6,822,461 B2  Page 1 of 1
DATED : November 23, 2004
INVENTOR(S) : Klun It is certified that error appears in the above-identified patent and that said Letters Patent is hereby corrected as shown below:

Column 3,
Line 55, after "itself" insert -- . --

Column 7,
Line 53, replace "device I" with -- device 1 --

Column 8,
Line 37, after "platinum" insert -- . --
Line 45, after "itself" insert -- , --

Column 10,
Line 62, after "itself" insert -- . --

Column 11,
Line 33, replace "claim 1" with -- claim 4 --

Signed and Sealed this

Second Day of August, 2005

JON W. DUDAS
*Director of the United States Patent and Trademark Office*